(12) United States Patent
Wang et al.

(10) Patent No.: US 12,019,674 B2
(45) Date of Patent: Jun. 25, 2024

(54) SYSTEM AND METHOD FOR TUMOR CHARACTERIZATION

(71) Applicant: NEW YORK UNIVERSITY, New York, NY (US)

(72) Inventors: Jing Wang, New York, NY (US); Prathamesh Kulkarni, New York, NY (US); Eric Robinson, Portland, OR (US)

(73) Assignee: New York University, New York, NY (US)

( * ) Notice: Subject to any disclaimer, the term of this patent is extended or adjusted under 35 U.S.C. 154(b) by 590 days.

(21) Appl. No.: 16/887,036

(22) Filed: May 29, 2020

(65) Prior Publication Data
US 2020/0381121 A1 Dec. 3, 2020

Related U.S. Application Data

(60) Provisional application No. 62/854,021, filed on May 29, 2019.

(51) Int. Cl.
*A61K 38/21* (2006.01)
*G06F 16/55* (2019.01)
(Continued)

(52) U.S. Cl.
CPC .......... *G06F 16/55* (2019.01); *G06F 18/2193* (2023.01); *G06F 18/2321* (2023.01);
(Continued)

(58) Field of Classification Search
CPC .. G06F 16/55; G06F 18/2193; G06F 18/2321; G06N 3/04; G06N 3/08;
(Continued)

(56) References Cited

U.S. PATENT DOCUMENTS

2017/0140533 A1 * 5/2017 Nelson ............... G01N 15/1468
2020/0380675 A1 * 12/2020 Golden ................. G06V 10/82

FOREIGN PATENT DOCUMENTS

CN 108027373 A * 5/2018 ............ G01N 21/31
WO WO-2015107722 A1 * 7/2015 ......... G06K 9/00127
(Continued)

OTHER PUBLICATIONS

Arvaniti et. al., "Automated Gleason grading of prostate cancer tissue microarrays via deep learning." Sci Rep 8, 12054 (2018).
(Continued)

*Primary Examiner* — Xin Jia
(74) *Attorney, Agent, or Firm* — Riverside Law LLP

(57) ABSTRACT

A method of treating a subject comprises administering a treatment to a subject identified as having a high probability of distant metastatic recurrence, wherein the probability of distant metastatic recurrence was determined by a process, comprising acquiring at least one image of a tissue sample comprising a plurality of cells, taken from a subject, classifying each of the plurality of cells into categories, dividing the at least one image into a plurality of patches, calculating values for a plurality of morphological features based on the patches, and calculating a distant metastatic recurrence probability based on the values. A computer-implemented method of training a neural network and a system for characterizing a cancer in a subject are also described.

10 Claims, 15 Drawing Sheets

(51) Int. Cl.
- G06F 18/21 (2023.01)
- G06F 18/2321 (2023.01)
- G06N 3/04 (2023.01)
- G06N 3/08 (2023.01)
- G06V 10/762 (2022.01)
- G06V 10/764 (2022.01)
- G06V 20/69 (2022.01)
- G16H 30/20 (2018.01)
- G16H 30/40 (2018.01)
- G16H 50/20 (2018.01)

(52) U.S. Cl.
CPC .............. G06N 3/04 (2013.01); G06N 3/08 (2013.01); G06V 10/763 (2022.01); G06V 10/764 (2022.01); G06V 20/693 (2022.01); G06V 20/698 (2022.01); G16H 30/20 (2018.01); G16H 30/40 (2018.01); G16H 50/20 (2018.01); G06V 2201/03 (2022.01)

(58) Field of Classification Search
CPC .......... G06N 3/044; G06N 3/045; G06N 5/01; G06N 20/20; G06N 3/082; G06V 10/763; G06V 10/764; G06V 20/693; G06V 20/698; G06V 2201/03; G16H 30/20; G16H 30/40; G16H 50/20
See application file for complete search history.

(56) References Cited

FOREIGN PATENT DOCUMENTS

| | | | | |
|---|---|---|---|---|
| WO | WO-2016138041 A2 * | 9/2016 | ......... | G01N 33/5011 |
| WO | WO-2018097678 A1 * | 5/2018 | ............... | C12Q 1/68 |

OTHER PUBLICATIONS

Bankhead et. al., "QuPath: Open source software for digital pathology image analysis." Sci Rep 7, 16878 (2017).
Bejnordi et. al., "Diagnostic Assessment of Deep Learning Algorithms for Detection of Lymph Node Metastases in Women With Breast Cancer." JAMA 318, 2199-2210 (2017).
Bejnordi et. al., "Using deep convolutional neural networks to identify and classify tumor-associated stroma in diagnostic breast biopsies." Mod Pathol 31, 1502-1512 (2018).
Bychkov et. al., "Deep learning based tissue analysis predicts outcome in colorectal cancer." Sci Rep 8, 3395 (2018).
Casanova et. al., "Morphoproteomic Characterization of Lung Squamous Cell Carcinoma Fragmentation, a Histological Marker of Increased Tumor Invasiveness." Cancer Res 77, 2585-2593 (2017).
Clemente et. al., "Prognostic value of tumor infiltrating lymphocytes in the vertical growth phase of primary cutaneous melanoma." Cancer 77, 1303-10 (1996).
Coudray et. al., "Classification and mutation prediction from non-small cell lung cancer histopathology images using deep learning." Nat Med 24, 1559-1567 (2018).
Delgado, et.al., "Sentinel Lymph Node Biopsy and Complete Lymph Node Dissection for Melanoma." Curr Oncol Rep 21, 54 (2019).
Elmore et. al., "Concordance and Reproducibility of Melanoma Staging According to the 7th vs 8th Edition of the AJCC Cancer Staging Manual." JAMA Netw Open 1 (2018).
Esteva et. al., "Dermatologist-level classification of skin cancer with deep neural networks." Nature 542, 115-118 (2017).
Ferris et. al., "Real-world performance and utility of a noninvasive gene expression assay to evaluate melanoma risk in pigmented lesions." Melanoma Res 28, 478-482 (2018).
Gartrell et. al., "Quantitative Analysis of Immune Infiltrates in Primary Melanoma." Cancer Immunol Res 6, 481-493 (2018).
Gartrell et. al., "Validation of Melanoma Immune Profile (MIP), a Prognostic Immune Gene Prediction Score for Stage II-III Melanoma." Clin Cancer Res 25, 2494-2502 (2019).
Gerami et. al., "Development of a prognostic genetic signature to predict the metastatic risk associated with cutaneous melanoma." Clin Cancer Res 21, 175-83 (2015).
Gordan, Blazer, Saundankar, et. al., "Cost differential of immuno-oncology therapy delivered at community versus hospital clinics." Am J Manag Care 25:e66-e70 (2019).
Henriques et. al., "The Emerging Therapeutic Landscape of Advanced Melanoma." Curr Pharm Des 24, 549-558 (2018).
Linder et. al., "Deep learning for detecting tumour-infiltrating lymphocytes in testicular germ cell tumours." J Clin Pathol. 72(2), 157-164 (Feb. 2019).
Lo et. al., "Artificial convolution neural network techniques and applications for lung nodule detection." IEEE Trans Med Imaging 14, 711-8 (1995).
Nir et. al., "Comparison of Artificial Intelligence Techniques to Evaluate Performance of a Classifier for Automatic Grading of Prostate Cancer From Digitized Histopathologic Images." JAMA Netw Open 2, e190442 (2019).
Palmieri et. al., "Immune Checkpoint Inhibitor Toxicity." Curr Oncol Rep 20:72 (2018).
Rizk et. al.. "Prognostic and Predictive Immunohistochemistry-Based Biomarkers in Cancer and Immunotherapy." Hematol Oncol Clin North Am 33, 291-299 (2019).
Saltz et. al., "Spatial Organization and Molecular Correlation of Tumor-Infiltrating Lymphocytes Using Deep Learning on Pathology Images." Cell Rep. 23(1), 181-193 (2018).
Shen et. al., "Deep Learning in Medical Image Analysis." Annu Rev Biomed Eng 19, 221-248 (2017).
Sivendran et. al., "Dissection of immune gene networks in primary melanoma tumors critical for antitumor surveillance of patients with stage II-III resectable disease." J Invest Dermatol 134, 2202-2211 (2014).
Srivastava et. al., "Dropout: A Simple Way to Prevent Neural Networks from Overfitting." Journal of Machine Learning Research 15, 1929-1958 (2014).
Taylor, Hood, Reisch, et. al., "Influence of variability in assessment of Breslow thickness, mitotic rate and ulceration among US pathologists interpreting invasive melanoma, for the purpose of AJCC staging." J Cutan Pathol 45, 588-596 (2018).
Trinidad, Torres-Cabala, Prieto, et. al., "Update on eighth edition American Joint Committee on Cancer classification for Merkel cell carcinoma and histopathological parameters that determine prognosis." J Clin Pathol 72, 337-340 (2019).
Wang et. al., "Prediction of recurrence in early stage non-small cell lung cancer using computer extracted nuclear features from digital H&E images." Sci Rep 7, 13543 (2017).
Weber et. al., "Adjuvant Nivolumab versus Ipilimumab in Resected Stage III or IV Melanoma." N Engl J Med 377, 1824-1835 (2017).
Xia et. al., "Computationally-Guided Development of a Stromal Inflammation Histologic Biomarker in Lung Squamous Cell Carcinoma." Sci Rep 8, 3941 (2018).

* cited by examiner

SYSTEM AND METHOD FOR TUMOR CHARACTERIZATION

CROSS-REFERENCE TO RELATED APPLICATIONS

This application claims priority to U.S. Provisional Patent Application No. 62/854,021, filed on May 29, 2019, incorporated herein by reference in its entirety.

BACKGROUND OF THE INVENTION

There is an urgent need to define prognostic biomarkers in early stage melanoma because, while effective adjuvant therapies to prevent recurrence and death are available, they incur significant toxicity and are very costly. Toxicity is tolerable in the advanced disease setting, but it is much less acceptable for otherwise healthy patients who have high probability of living a normal lifespan with good functional status if left untreated. Moreover, available treatments last up to a year or more and are extremely expensive. Given that death rates from melanoma at ten years range from 2%-8% for stage I disease, 12%-25% for stage II disease, and 12%-40% for stage III disease, treating all early stage melanoma patients would result in significant over-treatment and resource expenditure.

The current clinical criterion for evaluating risk of recurrence is the American Joint Committee on Cancer (AJCC) staging system. The AJCC staging system includes multiple parameters including depth of the primary tumor, ulceration, mitotic rate, and local or nodal metastasis. This system is highly useful but has several limitations. First, it does not account for the relative risk conferred by tumor depth and lymph node spread in that a deeper primary is deadlier than a small nodal metastasis, such that a stage IIIA patient has a better survival rate than does a stage IIC patient. Second, depth can be difficult to estimate accurately in some patients depending on technique, for example if a shave biopsy is performed or the original lesion is incompletely excised. Third, complete staging requires examination of lymph nodes, a procedure that is invasive and confers no survival benefit. In order to avoid surgery, patients are therefore in some situations incompletely staged. More precise and broadly applicable staging systems are needed to supplement AJCC staging.

Traditionally, characterization of genomic and proteomic features of primary melanoma tumors has been challenging because the very small size of these tumors necessitates that the entire specimen be formalin fixed and paraffin embedded (FFPE) in almost all circumstances to allow for review by an expert pathologist. Fortunately, newer technologies including the NanoString assay and specialized RNA sequencing methods coupled with quantitative multiplexed immunefluorescence (QIF) assays have allowed for quantification of RNA transcripts and phenotyping of immune cells within the tumor micro-environment. Recent developments in the field of melanoma include genomic signatures, and, most recently, a QIF-based biomarker consisting of the ratio of CD8+ T cells to CD68+ macrophages in tumor stroma. (see e.g. Linder et al.: Deep learning for detecting tumour-infiltrating lymphocytes in testicular germ cell tumours. J Clin Pathol 72:157-164, 2019, Saltz et al., Spatial Organization and Molecular Correlation of Tumor-Infiltrating Lymphocytes Using Deep Learning on Pathology Images. Cell Rep. 2018; 23(1):181-193, Xia et al: Computationally-Guided Development of a Stromal Inflammation Histologic Biomarker in Lung Squamous Cell Carcinoma. Sci Rep 8:3941, 2018, and Ehteshami Bejnordi B, Mullooly M, Pfeiffer R M, et al: Using deep convolutional neural networks to identify and classify tumor-associated stroma in diagnostic breast biopsies. Mod Pathol 31:1502-1512, 2018, all of which are incorporated herein by reference in their entireties). While these methods show promise, application can be challenging due to complex analysis methods not typically in use in clinical laboratories.

Meanwhile, the application of artificial intelligence (AI) to health care promises to substantially alter how medical care is delivered in the coming decades. While initial applications were primarily outside of medicine, machine learning has been successfully applied in multiple health care contexts including interpretation of imaging data for segmentation of anatomical features from MM data and diagnosis of skin lesions. (see e.g. Esteva et al: Dermatologist-level classification of skin cancer with deep neural networks. Nature 542:115-118, 2017, incorporated herein by reference). Most recently, machine learning has been applied to pathology imaging, notably to the identification of lymph node metastasis in breast cancer. (see Ehteshami et al: Diagnostic Assessment of Deep Learning Algorithms for Detection of Lymph Node Metastases in Women With Breast Cancer. JAMA 318:2199-2210, 2017, incorporated herein by reference). Developing prognostic biomarkers represents a unique challenge because pathologists generally diagnose rather than prognosticate, as prognostication generally includes multiple clinical parameters and is most frequently performed as a collaborative effort between pathologists and clinicians who have interactions with patients in an office setting.

Deep learning, a subset of machine learning, allows a computer to select ways of identifying patterns correlating with a defined outcome. Convolutional neural networks (CNN) are a specific type of deep learning well suited to image analysis tasks that require prediction based on smaller image patches. (see e.g. Shen et al.: Deep Learning in Medical Image Analysis. Annu Rev Biomed Eng 19:221-248, 2017, incorporated herein by reference). Deep learning techniques and CNN in particular have been applied to more complex problems in pathology such as identification of tumor infiltrating lymphocytes (TILs) and, more broadly, characterization of the tumor immune microenvironment. Further, deep learning promises to offer rapid and efficient methods to identify tumor subsets, correctly "grade" tumors based on cellular atypia, and "predict" gene mutations.

Thus, there is a need in the art for an improved method to predict visceral recurrence of DSS in subjects with a variety of primary cancers that is easier, less costly, and lower risk than existing methods, in order to avoid over-treatment of patients with early-stage cancers. The present invention satisfies this need.

SUMMARY OF THE INVENTION

In one aspect, a method of treating a subject comprises administering a treatment to a subject identified as having a high probability of distant metastatic recurrence, wherein the probability of distant metastatic recurrence was determined by a process, comprising acquiring at least one image of a tissue sample comprising a plurality of cells, taken from a subject, classifying each of the plurality of cells into categories, dividing the at least one image into a plurality of patches, calculating values for a plurality of morphological features based on the patches, and calculating a distant metastatic recurrence probability based on the values.

In one embodiment, the patches are acquired at least in part by random sampling. In one embodiment, the categories comprise tumor cells, non-tumor cells, or immune cells. In one embodiment, the process further comprises identifying regions of the image in which no cells appear and discarding those regions. In one embodiment, the process further comprises identifying regions of the image in which no tumor cells appear and discarding those regions. In one embodiment, the distant metastatic recurrence probability is calculated by at least one neural network. In one embodiment, the patches are selected by calculating a cell density and comparing the cell density to a threshold.

In one embodiment, the morphological features comprise at least one of (Count of immune cells in "large" cluster)/(Total count of immune cells); (Count of immune cells in "large" cluster)/(Total count of tumor+immune); (Count of immune cells in "large" cluster)/(Count of tumor cells in "large" cluster); (Count of immune cells in "large" cluster)/(Count of immune cells in "small" cluster); (Total count of immune cells)/(Total count of tumor+immune); (Immune cell total area)/(Tumor cell total area); and (Immune cell total area)/(Total Immune area+Tumor area). In one embodiment, the distant metastatic recurrence probability is calculated by aggregating a set of votes for each patch in the plurality of patches based on the values. In one embodiment, the at least one image comprises at least first and second images, the first and second images acquired from different body regions of the subject. In one embodiment, the treatment is selected from the group consisting of Nivolumab, Pembrolizumab, Ipilimumab, Dabrafenib, Trametinib, Vemurafenib, high-dose interferon alfa, chemotherapy, surgical excision, and immunotherapy.

In another aspect, a computer-implemented method of training a neural network for characterizing a cancer in a subject comprises acquiring at least one image of a tissue sample comprising a plurality of cells, taken from a subject, classifying each of the plurality of cells into categories, dividing the at least one image into a plurality of patches at least partially by random sampling, discarding patches having no tumor cell information from the plurality of patches, calculating values for a plurality of morphological features based on the patches, and training at least one neural network using a combination of the values and a low-dimensional representation of a sequence generated by a DNN.

In one embodiment, the patches have a size between 100×100 and 1000×1000. In one embodiment, the method further comprising the step of down sampling at least one of the plurality of patches. In one embodiment, the binary classifier is distant metastatic recurrence. In one embodiment, the morphological features comprise at least one of (Count of immune cells in "large" cluster)/(Total count of immune cells); (Count of immune cells in "large" cluster)/(Total count of tumor+immune); (Count of immune cells in "large" cluster)/(Count of tumor cells in "large" cluster); (Count of immune cells in "large" cluster)/(Count of immune cells in "small" cluster); (Total count of immune cells)/(Total count of tumor+immune); (Immune cell total area)/(Tumor cell total area); and (Immune cell total area)/(Total Immune area+Tumor area).

In another aspect, a system for characterizing a cancer in a subject comprises a non-transitory computer-readable medium with instructions stored thereon, that when executed by a processor perform steps comprising acquiring at least one image of a tissue sample comprising a plurality of cells affected by a cancer, taken from a subject, classifying each of the plurality of cells into categories, dividing the at least one image into a plurality of patches at least partially by random sampling, discarding patches having no tumor cell information from the plurality of patches, assembling the patches into a plurality of sequences, calculating values for a plurality of morphological features based on the sequences of patches, calculating a low-dimensional representation of the sequences using a DNN, and calculating an estimated characteristic of the cancer based on a combination of the values and the low-dimensional representation.

In one embodiment, the estimated characteristic is calculated by at least one neural network. In one embodiment, the characteristic is a probability of distant metastatic recurrence. In one embodiment, the steps further comprise calculating a plurality of binary values for the characteristic, wherein the estimated characteristic is an aggregate of the binary values. In one embodiment, the cancer is melanoma.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION

Figure 1A:
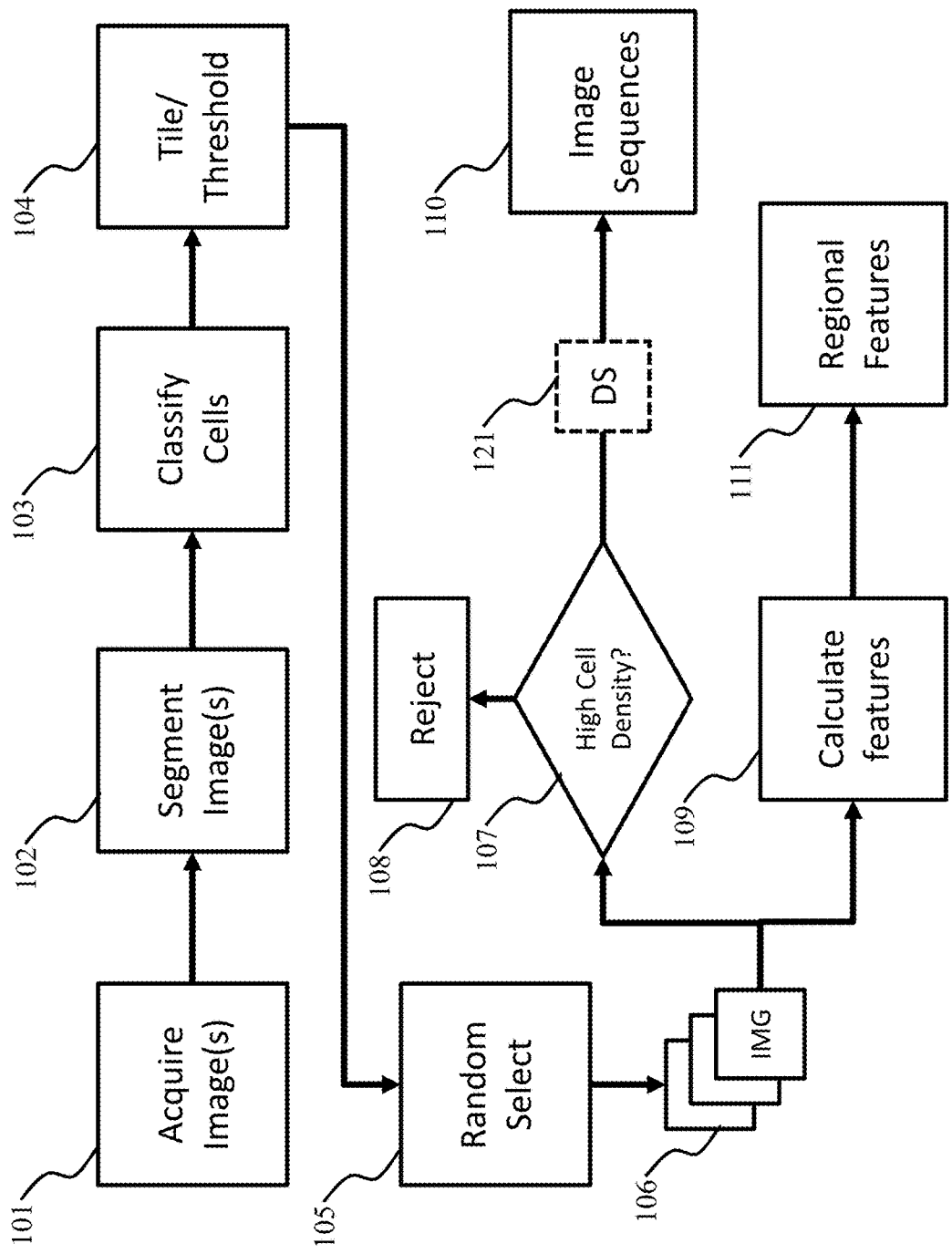
FIG. 1A, FIG. 1B, and FIG. 1C are an exemplary data pipeline of the present invention.

It is to be understood that the figures and descriptions of the present invention have been simplified to illustrate elements that are relevant for a clear understanding of the present invention, while eliminating, for the purpose of clarity, many other elements found in related systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C#, Objective-C, Java, JavaScript, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G, 4G/LTE, or 5G networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

As used herein, the term "diagnosis" refers to the determination of the presence of a disease or disorder. In some embodiments of the present invention, methods for making a diagnosis are provided which permit determination of the presence of a particular disease or disorder.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

Unless otherwise specified, scale bars included in figures of the present disclosure are 1 μm in length.

Aspects of the invention relate to a machine learning algorithm, machine learning engine, or neural network. A neural network may be trained based on various attributes of one or more tissue images, and may output one or more predictive probabilities based on the attributes. The resulting predictive probabilities may then be judged according to one or more binary classifiers or quality metrics, for example predictive accuracy of actual patient outcomes, and the weights of the attributes may be optimized to maximize the accuracy of the binary classifiers or quality metrics. In this manner, a neural network can be trained to predict and optimize for any binary classifier or quality metric that can be experimentally measured. In some embodiments, the neural network may have multi-task functionality and allow for simultaneous prediction and optimization of multiple quality metrics.

In embodiments that implement such a neural network, a query may be performed in various ways. A query may request the neural network identify a predictive probability related to a subject, for example distant metastatic recurrence. A neural network of the present invention may identify one or more predictive probabilities (as evaluated by the neural network) above a predetermined threshold, thereby indicating that one or more treatments or therapies should be administered to the subject. As contemplated herein, a predictive probability may be any prediction about any attribute of a cancer in subject.

In some embodiments, the neural network may be updated by training the neural network using a value of the desirable parameter associated with an input tissue image. Updating the neural network in this manner may improve the ability of the neural network in proposing optimal predictive probabilities. In some embodiments, training the neural network may include using a value of the desirable parameter associated with a known patient outcome. For example, in some embodiments, training the neural network may include predicting a value of the parameter for a tissue image, comparing the predicted value to the corresponding value associated with a known patient outcome, and training the neural network based on a result of the comparison. If the predicted value is the same or substantially similar to the observed value, then the neural network may be minimally updated or not updated at all. If the predicted value differs from that of the known patient outcome, then the neural network may be substantially updated to better correct for this discrepancy. Regardless of how the neural network is retrained, the retrained neural network may be used to propose additional predicted probabilities.

Although the techniques of the present application are in the context of distant metastatic recurrence, it should be appreciated that this is a non-limiting application of these techniques as they can be applied to other types of parameters or attributes, for example identifying patients who should not receive treatment, or identifying patients who would benefit from more aggressive adjuvant therapy. Depending on the type of data used to train the neural network, the neural network can be optimized for different types of cancer/tumor attributes.

Querying the neural network may include inputting one or more initial tissue images. The neural network may have been previously trained using different tissue images. The query to the neural network may be for a predictive probability related to one or more aspects of the cancer or tumor. A binary or probability value may be received from the neural network in response to the query.

The techniques described herein associated with iteratively querying a neural network by inputting one or more tissue images, receiving an output from the neural network including a predictive probability, and successively providing one or more additional images from the same subject as an input to the neural network, can be applied to other machine learning applications. Such techniques can be generalized for identifying a series of discrete attributes by applying a model generated by a neural network trained using data relating the discrete attributes to a characteristic of a series of the discrete attributes.

The following abbreviations may be used herein. DMR: distant metastatic recurrence; DSS: disease-specific survival; NED: no evidence of disease; OS: overall survival; DNN: deep neural network; CNN: convolutional neural network; RNN: recurrent neural network.

Some embodiments of the present invention may be presented herein in relation to melanoma, but it should be understood that the devices and methods discussed herein may be used with any cancer, including but not limited to breast cancer, ovarian cancer, prostate cancer, lung cancer, multiple myeloma, biliary cancer, and pancreatic cancer.

Embodiments of the invention provide methods for assessing the risk for cancer recurrence in a subject. Some embodiments include methods for identifying subjects who have an increased or enhanced risk for cancer recurrence and subjects who do not have an enhanced risk for cancer recurrence by detection of the biomarker disclosed herein.

These biomarkers may also be useful for monitoring subjects undergoing treatments and therapies for cancer, subjects who have had cancer, and subjects who are in remission. These biomarkers may also be useful for selecting or modifying therapies and treatments that would be efficacious in subjects having cancer, subjects who have had cancer, or subjects who are in remission.

Embodiments of the invention provide improved methods for assessing the risk for cancer recurrence. The risk for cancer recurrence can be assessed by measuring one or more of the biomarkers described herein, and comparing the measured values to comparator values, reference values, or index values. Such a comparison can be undertaken with mathematical algorithms or formulas in order to combine information from results of multiple individual biomarkers and other parameters into a single measurement or index.

Subjects identified as having an enhanced risk for recurrence can optionally be selected to receive treatment regimens, such as radiotherapy or administration of therapeutic compounds to prevent, treat or delay the recurrence of cancer.

Identifying a subject as having an enhanced risk for cancer recurrence allows for the selection and initiation of various therapeutic interventions or treatment regimens in order to delay, reduce or prevent recurrence in those at risk. Further, identifying a subject with a low risk, or those who do not have an enhanced risk, for cancer recurrence allows for the sparing of unneeded additional therapy administered to the subject.

Monitoring the levels of at least one biomarker also allows for the course of treatment to be monitored. For example, a sample can be provided from a subject undergoing treatment regimens or therapeutic interventions. Such treatment regimens or therapeutic interventions can include surgery, radiation, chemotherapy, and the like.

Some biomarkers disclosed herein can thus be used to generate a biomarker profile or signature of the subjects: (i) who have an increased risk for cancer recurrence, (ii) who do not have an increased risk for cancer recurrence, and/or (iii) who have a low risk for cancer recurrence. The biomarker profile of a subject can be compared to a predetermined or comparator biomarker profile or reference biomarker profile to assess the risk for cancer recurrence. Data concerning the biomarkers of the present invention can also be combined or correlated with other data or test results, such as, without limitation, measurements of clinical parameters or other algorithms for cancer recurrence. Other data includes age, ethnicity, primary tumor staging, lymph node staging, metastasis staging, and other genomic data, specifically expression values of other gene signatures relevant to cancer outcomes, and the like. The data may also comprise subject information such as medical history and any relevant family history.

One aspect of the invention is a biomarker that stratifies patients with early stage melanoma using information derived from computational analysis of images of stained (e.g. Hematoxylin and Eosin (H&E) stained) tissue, for example using a neural network, which in one embodiment is a DNN. The disclosed biomarker is easily applicable in a clinical context as in some embodiments it requires no additional tissue processing, such as RNA extraction or immunohistochemical staining. The biomarker was generated based on image analysis of a training set with DMR as the label distinguishing favorable from unfavorable outcomes. It was then found to correlate with DSS in two independent validation populations. In certain aspects, the analysis described herein is used to determine prognosis, aid in determining the stage of cancer in a subject, determine the risk of metastatic recurrence in a subject, identify a subject as a candidate for subsequent adjuvant therapy, and/or identifying a subject as a candidate for a clinical trial.

In some embodiments, a method of the present invention comprises the step of administering one or more treatments, for example but not limited to an adjuvant therapy based on a value of the disclosed biomarker. Exemplary adjuvant therapies include, but are not limited to checkpoint inhibitor immunotherapy, for example Nivolumab, Pembrolizumab, or Ipilimumab; a targeted therapy, for example Dabrafenib plus Trametinib or Vemurafenib; or a high-dose interferon alfa. In some embodiments, a treatment includes chemotherapy, surgical excision, or immunotherapies.

In one aspect, the present invention comprises an automated data pipeline taking as its input one or more images of cells. In one embodiment, H&E stained images may be used, but alternatives include, but are not limited to, sections that have been bleached to remove melanin and samples stained with antibodies labeled with fluorescent or chromagen-based labels. Images may be any suitable size and magnification, and in some embodiments multiple different images having different sizes and magnification levels may be used as inputs. In one embodiment, suitable image sizes include any size up to 4 GB, or about 80,000 pixels on long side, and suitable image magnification levels include 5×, 10×, 20×, 40×, 0.25 μm/pixel at 40× magnification. However, it is understood that any image size may be used. Images may be captured and stored in any suitable format, including but not limited to TIFF, BMP, RAW, SCN, SVS, VMS, VMU, NDPI, MRXS, SVSLIDE, or BIF. Images may be from the same or a different tumor, different cuts from the same tumor, different 2D slices, and/or from substantially the same or a different location in the body. As an output, the data pipeline produces a DMR status prediction as a numerical value, for example as a value between 0 (no DMR likelihood) and 1 (highest likelihood of DMR). Different thresholds may be used for determining whether a given DMR percentage is "likely," for example for one sample type a threshold may be 0.3, such that a returned value of 0.35 is classified as DMR likely. In another type of sample, the threshold may be 0.8, such that a returned value of 0.75 is classified as DMR not likely.

Figure 2:
FIG. 2 is a stained image of a tissue sample.
Figure 3:
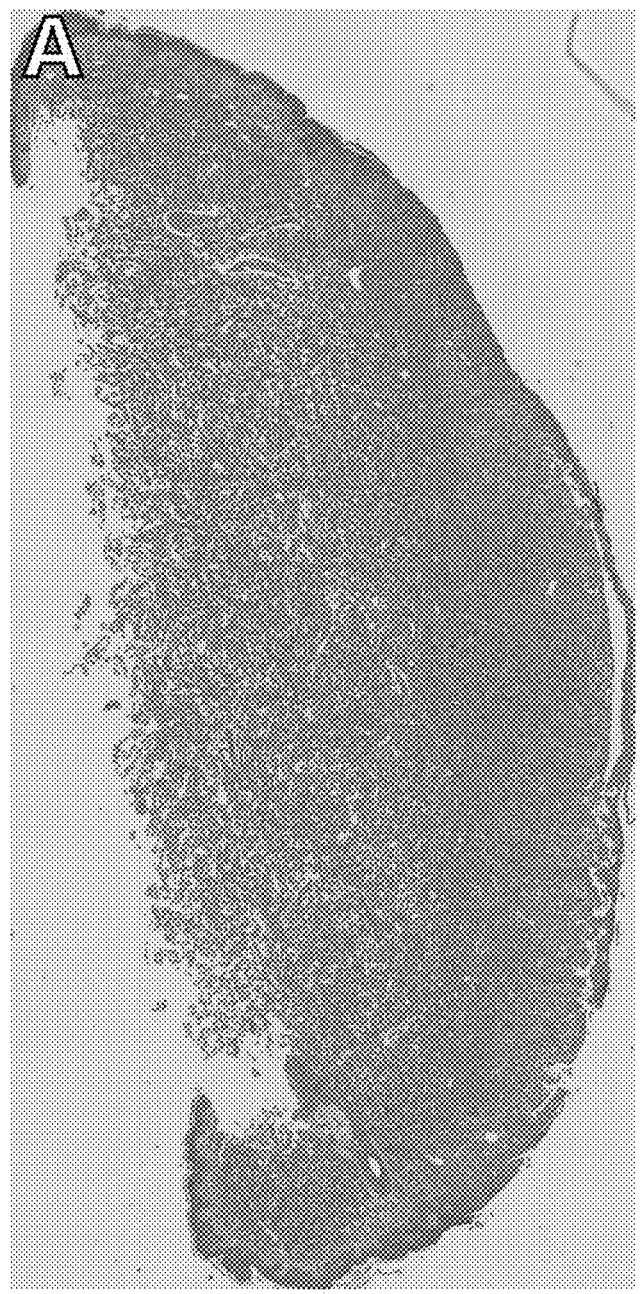
FIG. 3 is a processed image of a tissue sample.

A partial view of an exemplary data pipeline of the present invention is shown in FIG. 1A. Images are first acquired (and any applicable stains applied) in 101. Properly formatted images containing the relevant level of detail may be very large (1-15 gigabytes each), and so may therefore not be suitable for direct processing through a neural network. An exemplary sample image with an H&E stain applied is shown in FIG. 2. Due to the nature of the information being processed, sections of the image without nuclear information (e.g. connective tissue or areas outside the tissue sample) are not of interest, and so in step 102, the image is segmented into regions containing nuclear information (e.g. healthy or cancerous cells) and regions not containing nuclear information. Tumor information is necessary in some embodiments for an accurate recurrence prediction, and thus, in certain embodiments, image regions lacking cell information are omitted to reduce noise in the final output. Suitable methods for determining cell segmentation include, but are not limited to, edge detection, centroid detection, QuPath software, and/or OpenCV Watershed Cell Detection. An exemplary visual representation of a segmented image is shown in FIG. 3, with green regions denoting areas estimated to contain nuclear information.

Figure 4:
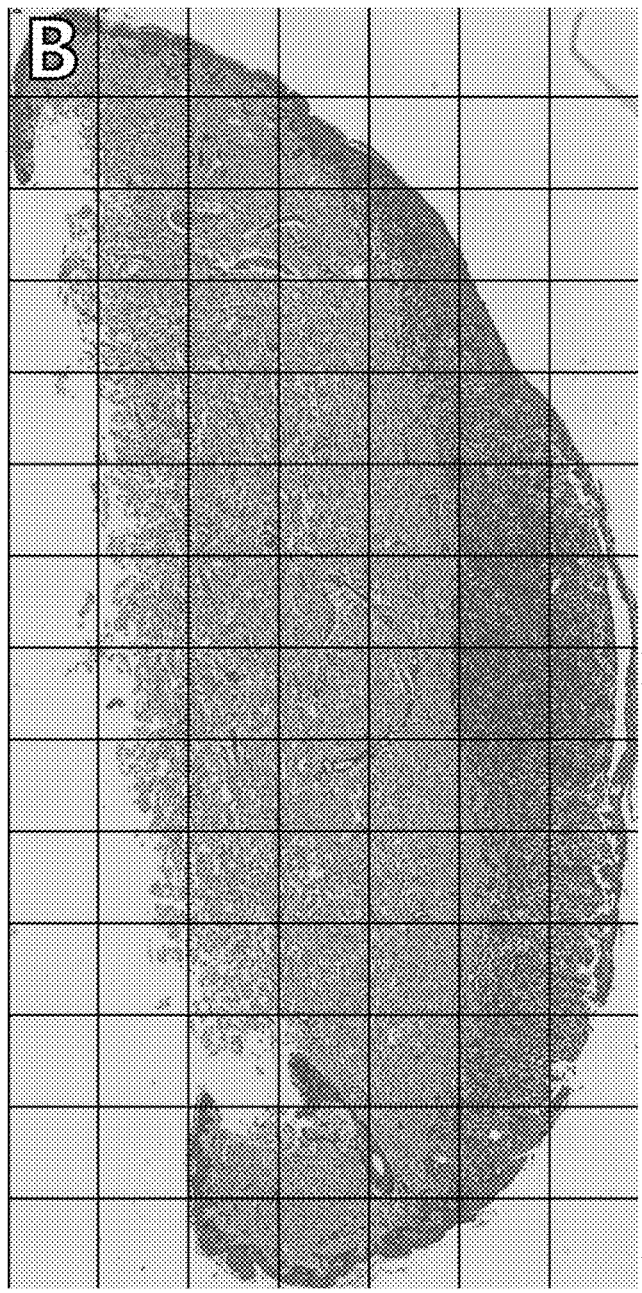
FIG. 4 is a processed image of a tissue sample.

Next, in step 103, the individual cells in the region containing nuclear information are classified into groups, for example as tumor cells, non-tumor cells, or immune cells. An exemplary classification is shown in FIG. 4, where red represents tumor cells, yellow represents immune cells, and blue represents non-cell regions. Suitable classification methods include the QuPath digital pathology software or other platforms.

In step 104, the image from FIG. 4 is segmented into a grid of fixed size, where each square in the grid (referred to interchangeably herein as a "tile") is configured for use as an input to a neural network. Suitable tile sizes are in the range of 500 px (5×100 patch size) to 10,000 px (2000 px patch size). Each tile is then evaluated and grid tiles having at least a minimum tumor and/or lymphocyte density are selected.

Figure 5:
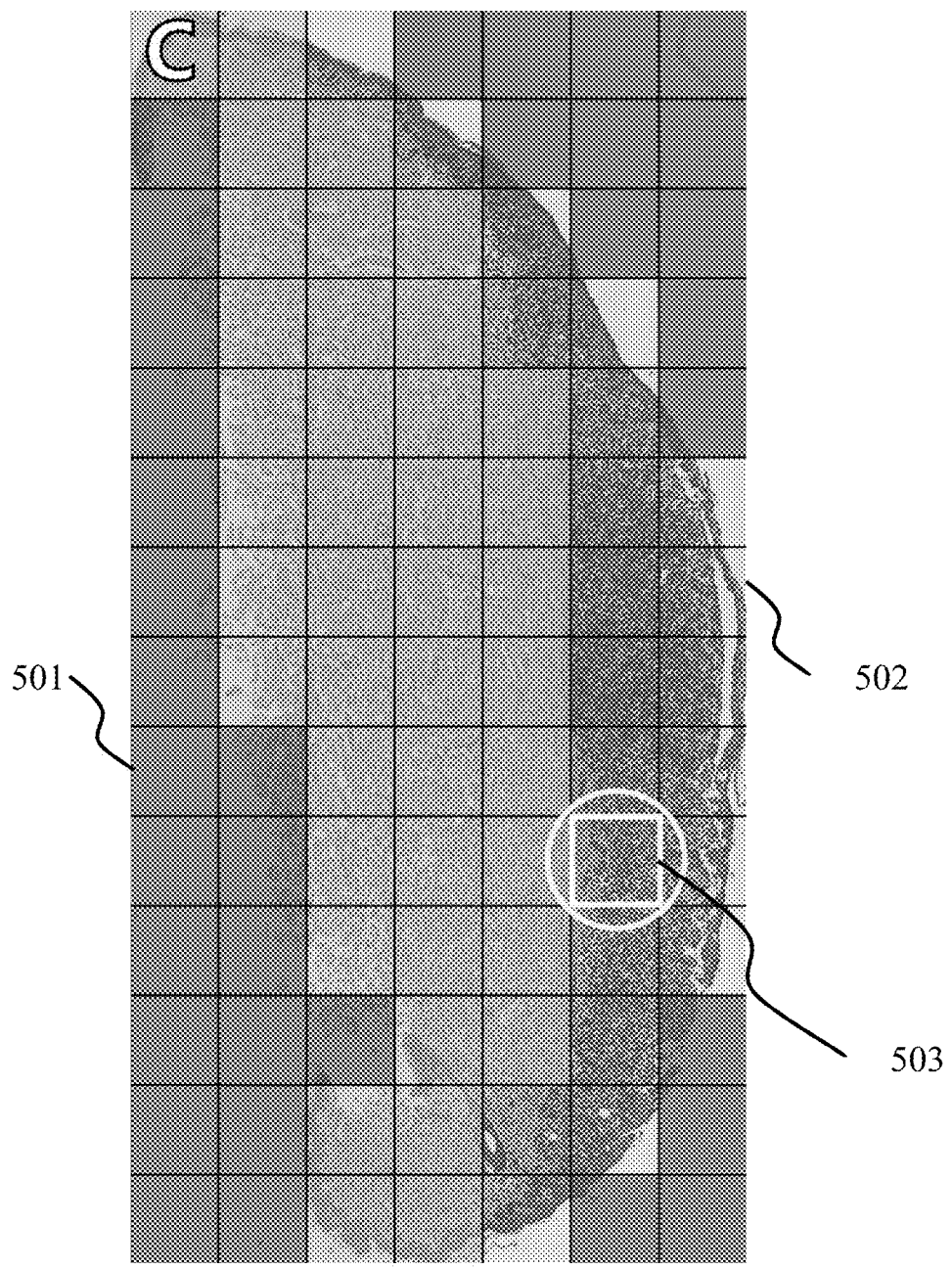
FIG. 5 is a processed image of a tissue sample.

With reference to the exemplary image in FIG. 5, tiles having no cell information, for example 501, are discarded. Tiles having a higher concentration of relevant information, such as 502 and 503, are retained.

Figure 6:
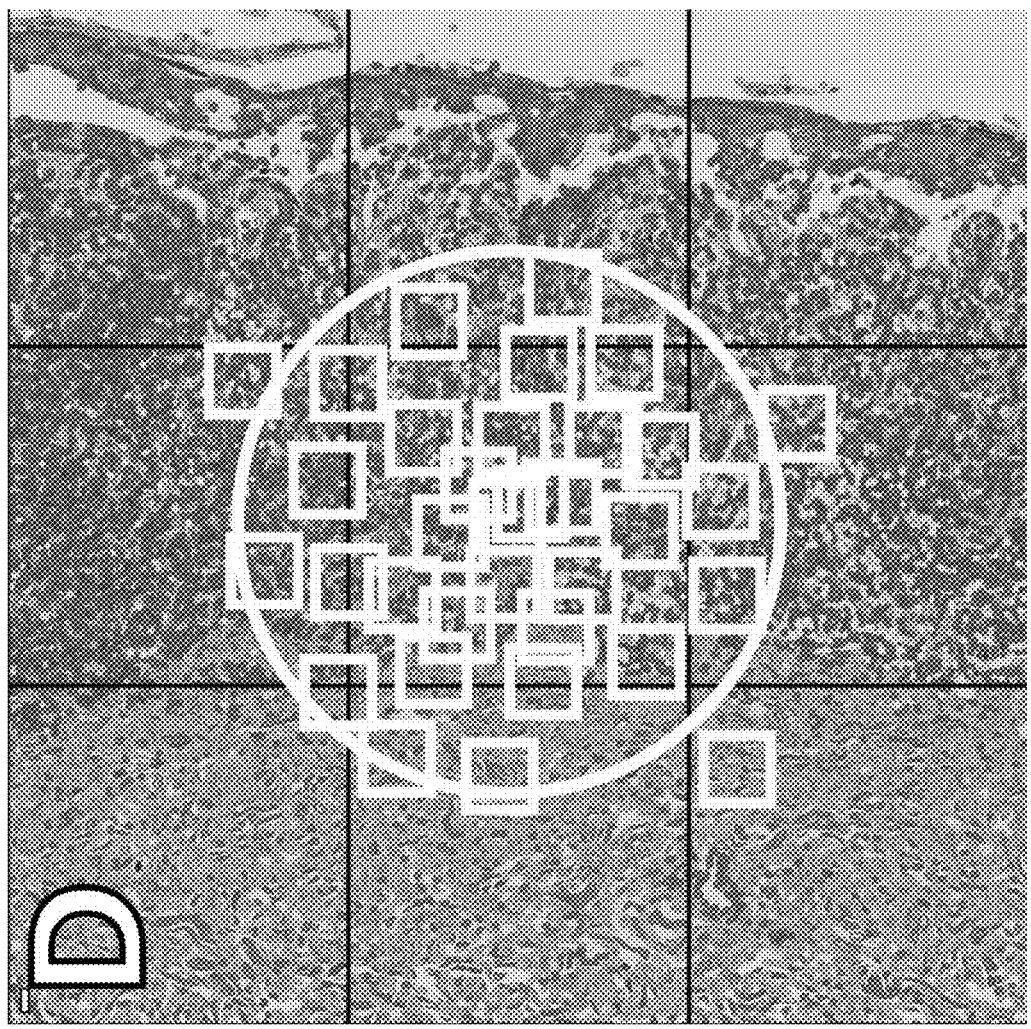
FIG. 6 is a diagram of a set of patches selected from a set of tiles.
Figure 7:
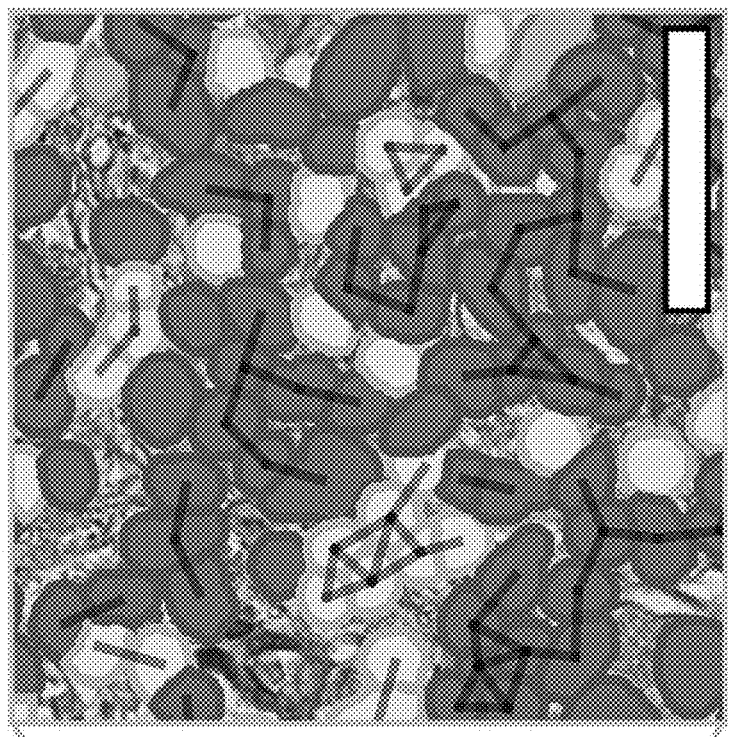
FIG. 7 is a detail view of a cell density diagram.
Figure 7:
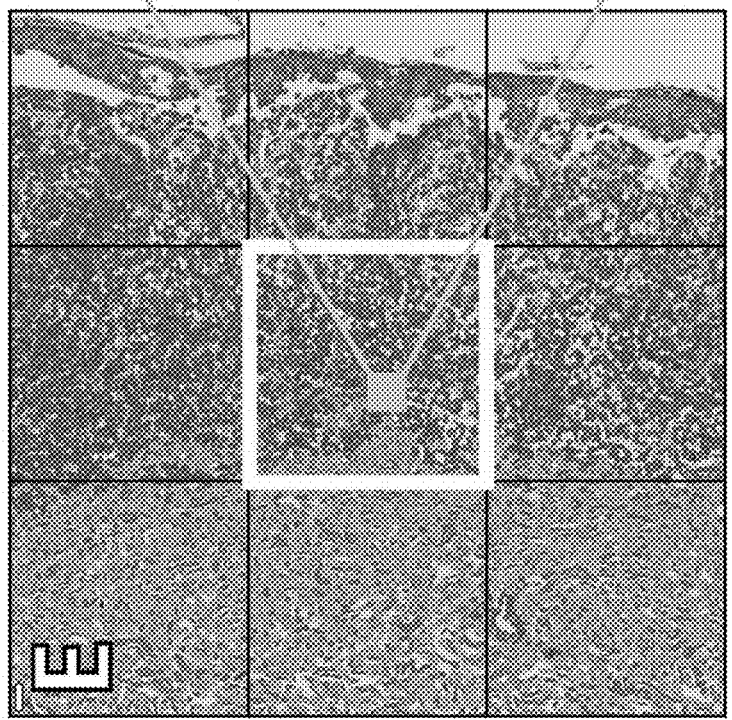

Next, in step 105, some or all of the tiles are randomly subsampled and a spatially localized, fixed- or variable-length sequences of patches 106 from each grid tile is selected (see e.g. FIG. 6). Suitable patch sizes include 100×100, 128×128, 500×500, 512×512, 1000×1000, and any size in between. In addition, regional image information is augmented with cell density features designed both to characterize the atypia of tumor cells and to summarize a larger immune infiltration context around each tile (step 109). The features are passed into the neural network via 111. An exemplary cell density feature characterization is shown in FIG. 7, where 702 is a detail view of the indicated region of 701. In some embodiments, regional image information may be further augmented with clustering information as shown in FIG. 7. Exemplary morphological features include, but are not limited to (Count of immune cells in "large" cluster)/(Total count of immune cells); (Count of immune cells in "large" cluster)/(Total count of tumor+immune); (Count of immune cells in "large" cluster)/(Count of tumor cells in "large" cluster); (Count of immune cells in "large" cluster)/(Count of immune cells in "small" cluster); (Total count of immune cells)/(Total count of tumor+immune); (Immune cell total area)/(Tumor cell total area); and (Immune cell total area)/(Total Immune area+Tumor area).

Figure 8:
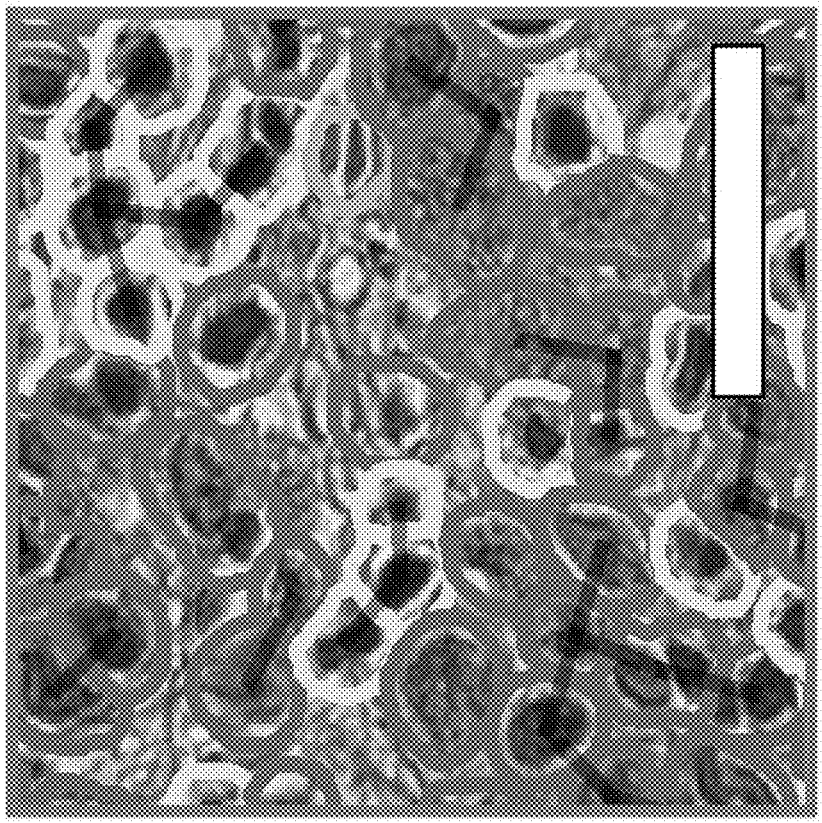
FIG. 8 is a detail view of exemplary dense cell regions.
Figure 8:
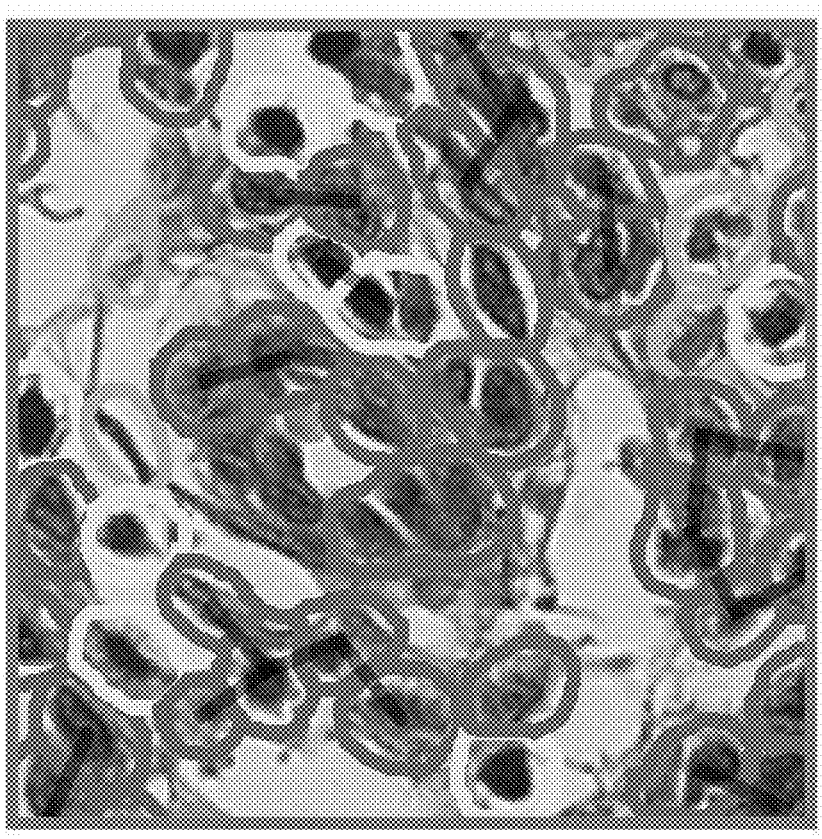
Figure 9:
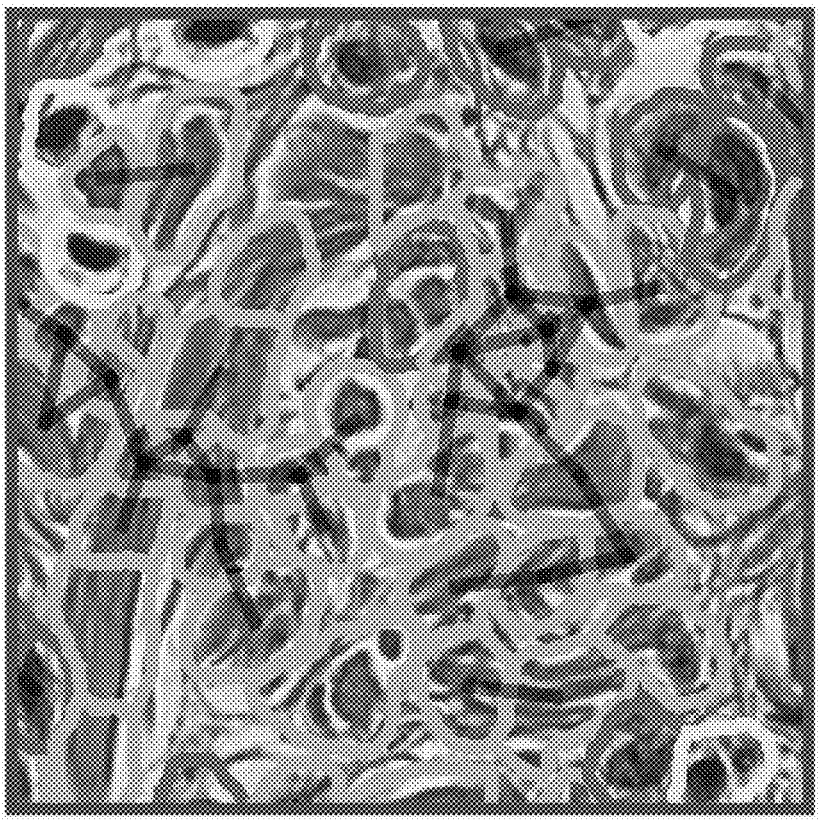
FIG. 9 is a detail view of exemplary less dense cell regions.
Figure 9:
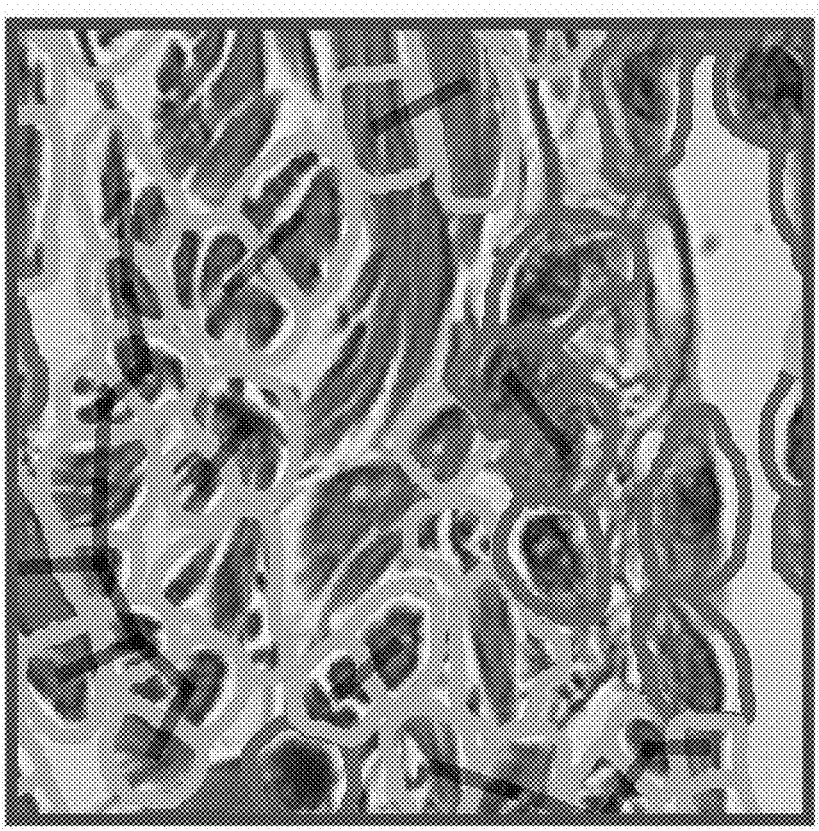
Figure 13:
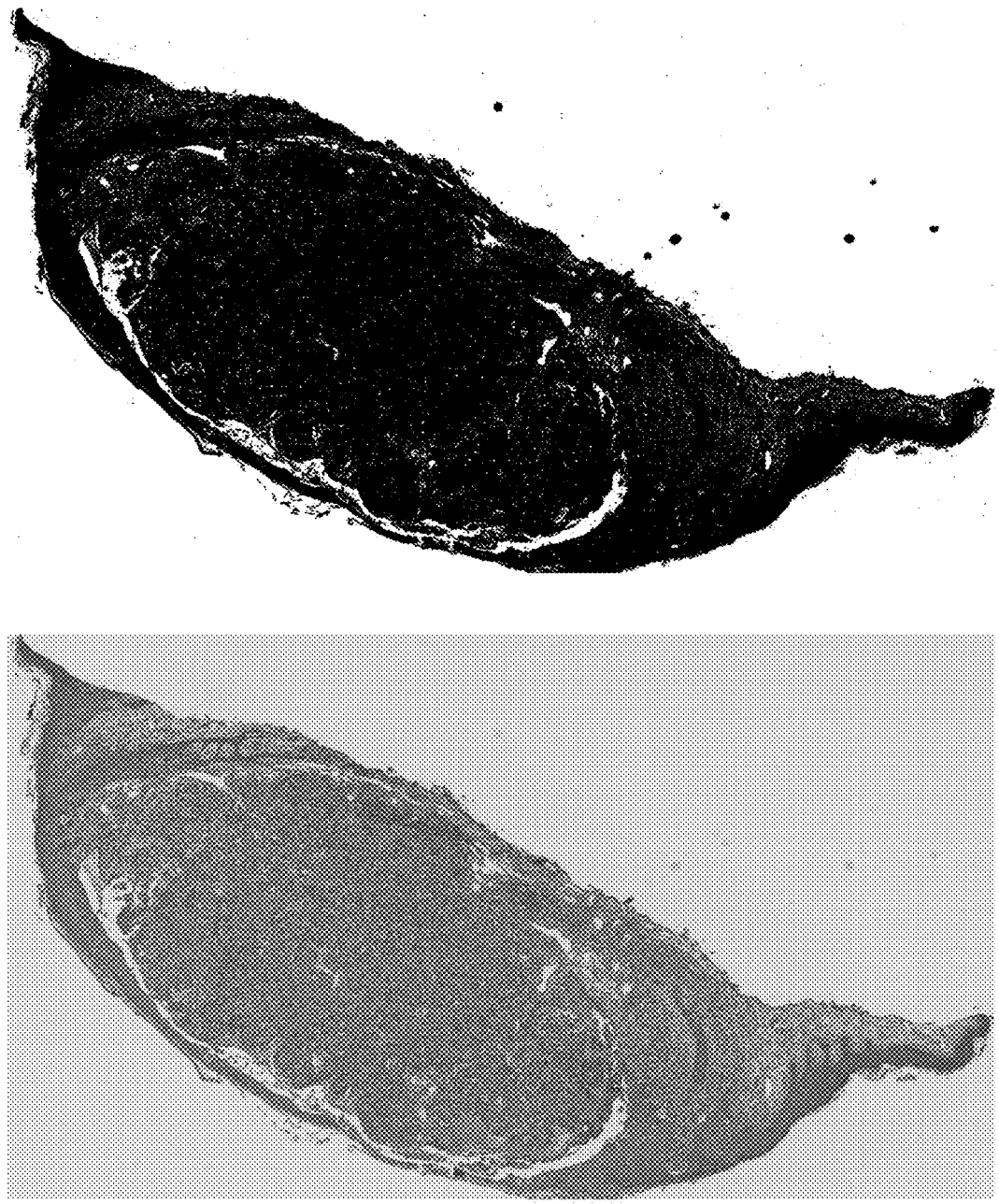
FIG. 13 is an exemplary binary mask.

Clustering may be calculated for example with a Delaunay clustering algorithm using a radius of one cell width, for example 40 px at 40× magnification. After Delaunay clustering, clusters are designated as "large" or "small" according to a threshold x, where if the number of cells in a cluster is greater than x, it is considered a "large" cluster, otherwise, it is a "small" cluster. The threshold size for a "large" or "small" cluster may be determined for example using a grid search, as shown generally in FIG. 11. Patches are evaluated in step 107 and those patches having high cell density are added to an image sequence in step 110, while patches having low cell density are discarded in step 108. Exemplary patches having high cell density are shown in FIG. 8, while exemplary patches having low cell density are shown in FIG. 9. Image sequences may have a length in a range of 2-100, or 2-50, or 5-30. In one embodiment, the image sequence length is 20 patches. In some embodiments, patches are optionally processed in image processing step 121, for example some or all of down sampling, background removal, or normalizing before being added to an image sequence. An exemplary background removal process includes the steps of setting a pixel threshold mask where the average pixel intensity value across RGB channels is above a threshold, for example 217. Where a pixel has an average value above the threshold, that pixel is set to (255,255,255) (white). Where a pixel has an average value below the threshold, that pixel may be set to (0,0,0) (black). An example of a binary mask is shown in FIG. 13. Suitable methods for determining which tiles to discard include use of a threshold, for example discarding tiles having more than 50% or 60% or 65% of raw image pixels as white space background (pixel intensity value above a threshold, for example 200 or 215 or 217); or above a threshold of segmented objects within the tile area classified as other, for example above 60% or above 70% or above 80% or above 85%. In this way, the neural network can be more efficient by evaluating only those regions of the image which are relevant to the outcome.

Figure 1B:
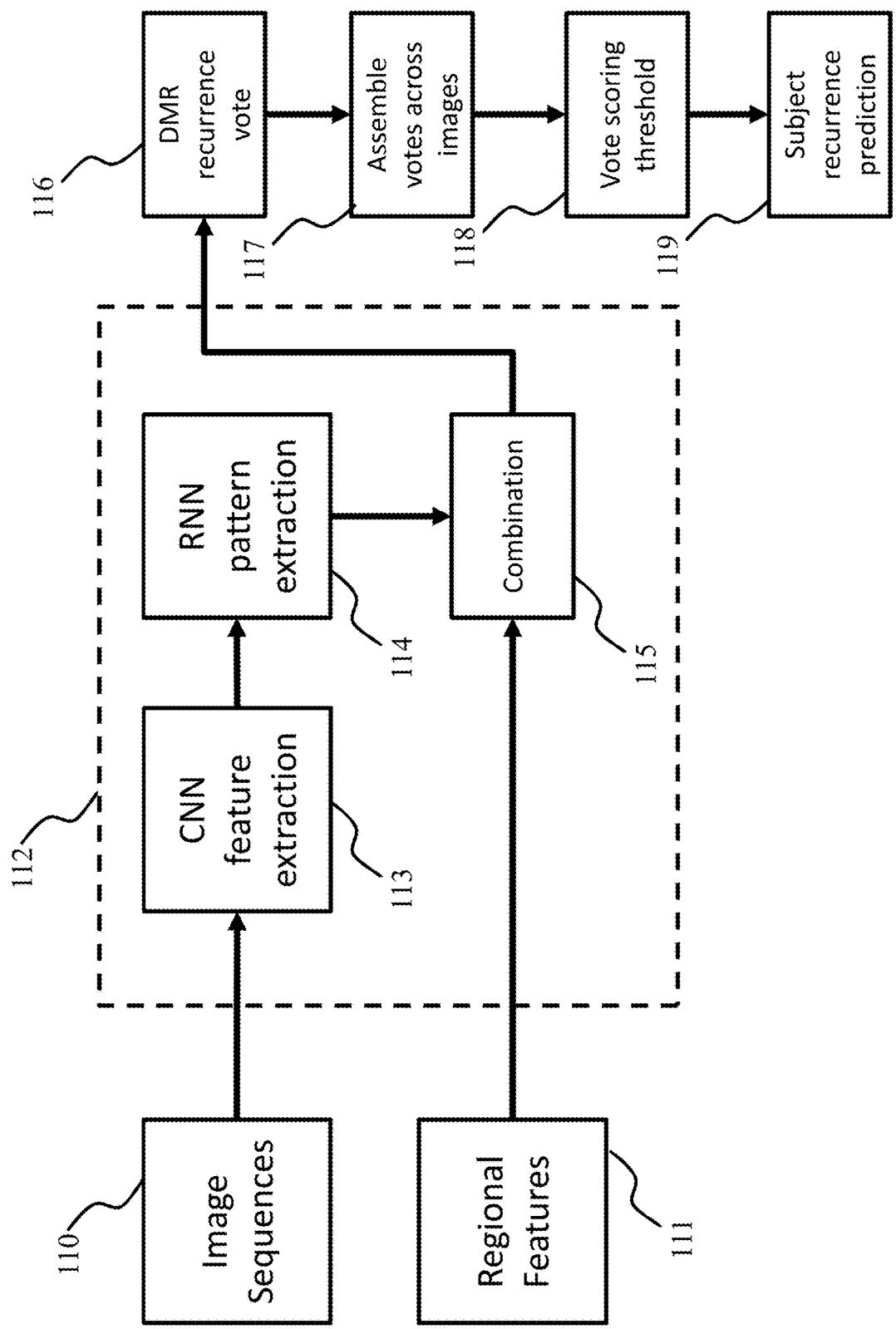

A second phase of a data pipeline is shown in FIG. 1B. A deep neural network 112 takes as its inputs the image sequences 110 comprising raw image data and the corresponding computed regional features 111. First, a CNN 113 (with one or more layers) extracts high-dimensional features from the individual patches in the image sequences 110. The CNN 113 may have between 1 and 10 layers, or between 1 and 3 layers, or between 3 and 5 layers, or between 2 and 8 layers, or any suitable number of layers. The results are run through a Recurrent Neural Network (RNN) with one or more layers and single- or bi-directional information flow, which processes the CNN output to identify discriminative spatial patterns. In one embodiment, the RNN is designed as a Long Short Term Memory network (LSTM). Finally, two fully connected layers 115 combine the output of the RNN with the pre-computed regional features 111 resulting in a softmax recurrence probability vote for every sequence. To generate the DMR probability 119 for each patient in the test set, individual votes 116 are aggregated 117 across all available subject images and the percentage of positively classified sequences are counted 118 to generate a final prediction score.

Figure 1C:
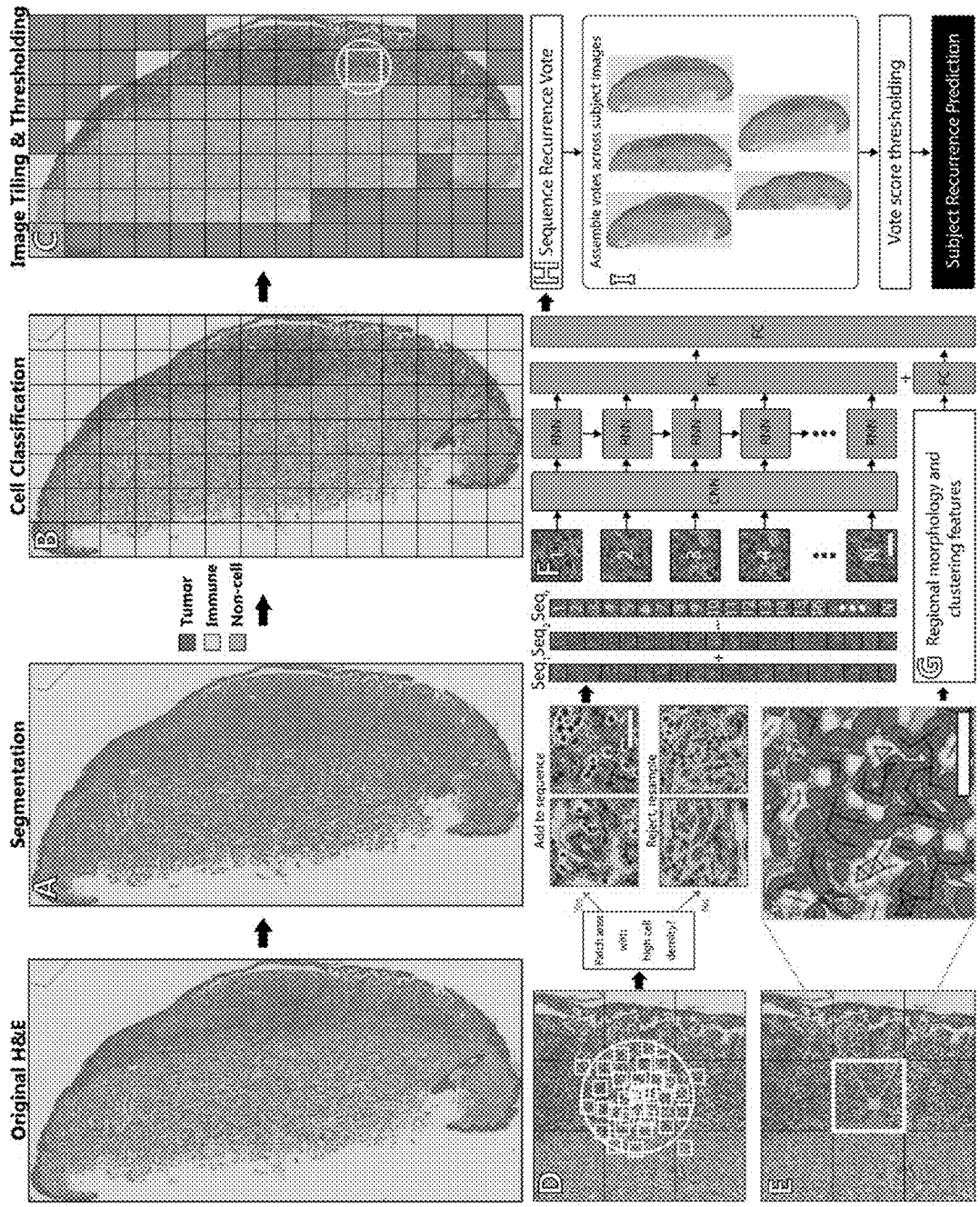

A summary diagram of the data pipeline disclosed in FIG. 1A and FIG. 1B is shown in FIG. 1C.

In the depicted data pipeline, a DMR probability for a subject is calculated based solely on the input images and the accompanying analysis, but in some embodiments, additional factors about the subject may be used, including but not limited to age, gender, race, tumor stage, tumor characteristics (size, location, depth, etc.), family history, genetic markers, and co-morbidity.

In one embodiment, the binary classifier used for training the neural networks is DMR, but in other embodiments, other binary classifiers may be used, for example one year survival, two year survival, five year survival, ten year survival, and local recurrence. The neural networks may be trained using various parameters, including a dropout rate in a range of 0.01-0.5 and a learning rate in a range of 1 e-6 to 1 e-2.

Figure 10:
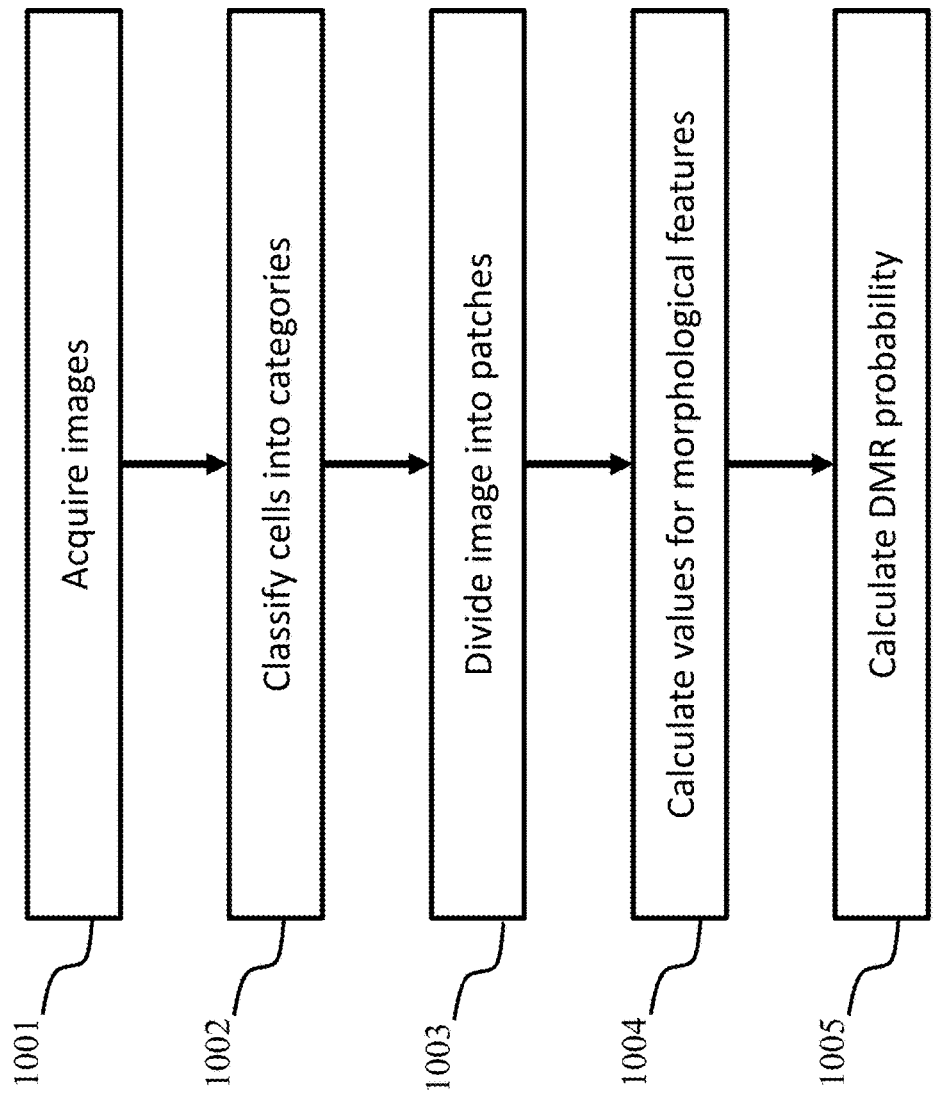
FIG. 10 is a method of the present invention.

With reference now to FIG. 10, a method of the present invention is shown. The method comprises the steps of acquiring at least one image of a tissue sample comprising a plurality of cells taken from a subject in step 1001, classifying each of the plurality of cells into categories in step 1002, dividing the at least one image into a plurality of patches in step 1003, calculating values for a plurality of morphological features based on the patches in step 1004, and calculating a distant metastatic recurrence probability based on the values in step 1005.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the system and method of the present invention. The following working examples therefore, specifically point out the exemplary embodiments of the present invention, and are not to be construed as limiting in any way the remainder of the disclosure.

This method was developed on an image base from 108 patients and applied to two independent validation sets of 104 and 51 patients respectively, yielding AUC values of 0.905 and 0.880. A cutoff selected based on the first validation set was tested in the second validation set and predicted DSS based on Kaplan Meier analysis ($p<0.0001$). This method is novel and rapidly applicable to standard clinical workflows and could be tested in the prospective setting for application to patient care.

Materials and Methods

Patients, Clinical Information, and Imaging

The training cohort was selected based on availability of H&E slides and clinical information. Patients from databases previously generated for the development and validation of melanoma immune profile (MIP) with at least one available H&E slide and 24 months of clinical follow up were included. Full patient demographics of the training cohort are provided in Table 1 below. Two validation cohorts were tested, the first consisting of 104 patients described in Table 2, and the second including 51 patients from described in Table 3. All slides were reviewed by a pathologist to confirm melanoma content. Slides were scanned using a Leica SCN 400 system with high throughput 384 slide autoloader (SL801) and tiff format files were generated. A separate image was generated for separate pieces of tissue on each slide as is frequently the case for primary melanomas due to tissue sectioning methods. Images were reviewed for quality and excluded due to excessive melanin obscuring cellular features or poor tissue quality. From the training set, 10 images were excluded for excessive melanin and one image was excluded for sample quality. From the validation cohort 2 set, four images were excluded for excessive melanin and one for lack of tumor. From the validation cohort 1 set, seven were excluded for excessive melanin and seven for sample quality.

TABLE 1

| (n = 108) | |
|---|---|
| Clinical characteristics | |
| Sex, n (%) | |
| Male | 73 (67.6) |
| Female | 34 (31.5) |
| Unknown | 1 (0.9) |
| Age | |
| Known, n (%) | 103 (95.4) |
| Median, n (range) | 67 (22-96) |
| Unknown, n (%) | 5 (4.6) |
| Location of tumor, n (%) | |
| Trunk | 58 (53.7) |
| Extremity | 48 (44.4) |
| Unknown | 2 (1.9) |
| Stage, n (%) | |
| I | 22 (20.4) |
| II | 62 (57.4) |
| III | 24 (22.2) |
| Pathologic characteristics | |
| Depth (mm) | |
| Median, n (range) | 2.30 (0.30-30) |
| Ulceration, n (%) | |
| Absent | 57 (52.8) |
| Present | 47 (43.5) |
| Unknown | 4 (3.7) |

TABLE 1-continued

| (n = 108) | |
|---|---|
| Microsatellite lesions, n (%) | |
| Absent | 101 (93.5) |
| Present | 6 (5.6) |
| Unknown | 1 (0.9) |
| SLNB status, n (%) | |
| Completed | 66 (61.1) |
| Positive, n (% of completed) | 20 (18.5) |
| Negative, n (% of completed) | 46 (42.6) |
| Not completed | 15 (13.9) |
| SLNB status unknown | 27 (25) |
| Outcome characteristics | |
| Patient follow-up (months) | |
| Median, n (range) | 58 (7-173) |
| DMR (months), n (%) | |
| Distant recurrence | 34 (31.5) |
| No recurrence or local recurrence only | 74 (68.5) |
| OS (months), n (%) | |
| Alive (at least 2 years) | 69 (63.9) |
| Dead | 39 (36.1) |
| DSS (months), n (%) | |
| Alive or NED at death | 78 (72.2) |
| Dead with melanoma | 30 (27.8) |

TABLE 2

| (n = 104) | |
|---|---|
| Clinical characteristics | |
| Sex, n (%) | |
| Male | 52 (50.0) |
| Female | 52 (50.0) |
| Age | |
| Median, n (range) | 60 (25-86) |
| T-stage, n (%) | |
| T1a or T1b | 23 (22.1) |
| T2a | 12 (11.5) |
| T2b or T3a | 31 (29.8) |
| T3b or T4a | 22 (21.2) |
| T4b | 14 (13.5) |
| Unknown | 2 (1.9) |
| Pathologic characteristics | |
| Depth (mm) | |
| Median, n (range) | 2.35 (0.15-8.30) |
| Ulceration, n (%) | |
| Absent | 63 (60.6) |
| Present | 39 (37.5) |
| Unknown | 2 (1.9) |
| Microsatellite lesions, n (%) | |
| Absent | 75 (72.1) |
| Present | 27 (26.0) |
| Unknown | 2 (1.9) |
| Outcome characteristics | |
| Patient follow-up (months) | |
| Median, n (range) | 71.2 (1.4-456.2) |
| OS (months), n (%) | |
| Alive (at least 2 years) | 26 (25.0) |
| Dead | 78 (75.0) |

TABLE 2-continued

| (n = 104) | |
|---|---|
| DSS (months), n (%) | |
| Alive or NED at death | 58 (55.8) |
| Dead with melanoma | 46 (44.2) |

TABLE 3

| (n = 51) | |
|---|---|
| Clinical characteristics | |
| Sex, n (%) | |
| Male | 27 (52.9) |
| Female | 24 (47.1) |
| Age | |
| Median, n (range) | 67 (20-90) |
| Location of tumor, n (%) | |
| Trunk | 31 (60.8) |
| Extremity | 20 (39.2) |
| Stage, n (%) | |
| II | 25 (49.0) |
| III | 26 (51.0) |
| Pathologic characteristics | |
| Depth (mm) | |
| Median, n (range) | 3.45 (0.65-13) |
| Ulceration, n (%) | |
| Absent | 23 (45.1) |
| Present | 28 (54.9) |
| Microsatellite lesions, n (%) | |
| Absent | 43 (84.3) |
| Present | 7 (13.7) |
| Unknown | 1 (2.0) |
| SLNB status, n (%) | |
| Completed | 47 (92.2) |
| Positive, n (% of completed) | 19 (40.4) |
| Negative, n (% of completed) | 28 (59.6) |
| Not completed | 4 (7.8) |
| Outcome characteristics | |
| Patient follow-up (months) | |
| Median, n (range) | 56 (9-142) |
| DMR (months), n (%) | |
| Distant recurrence | 29 (56.9) |
| No recurrence or local recurrence only | 22 (43.1) |
| OS (months), n (%) | |
| Alive (at least 2 years) | 22 (43.1) |
| Dead | 29 (56.9) |
| DSS (months), n (%) | |
| Alive or NED at death | 25 (49.0) |
| Dead with melanoma | 19 (37.3) |
| Unknown | 7 (13.7) |

Binary Classifier Selection

To generate a binary classifier for training, patients in the training set were characterized based on whether they developed distant metastatic recurrence (DMR). The DMR endpoint was selected because death rates from melanoma have decreased over the past decade due to fundamental advances in immunotherapy such that, fortunately, patients diagnosed today are more likely to survive. Thus, over time DMR is a more consistent reflection of biology than is survival. Effective adjuvant therapy, however was not introduced into general practice until 2017 with the FDA approval of nivolumab for resected stage III melanoma. Therefore, the time to distant metastatic recurrence has remained consistent until very recently. Further, patients with local recurrence are at significantly lower risk of dying of melanoma and remain in the stage III category and thus patients who only developed local recurrence over the course of follow up were characterized into the favorable group provided they had 24 months of recurrence-free clinical follow up after the local recurrence. Thus, the label was designed to distinguish patients with aggressive melanoma from those at low risk of death from disease.

Identification of Regions of Interest

In order to isolate tumor and immune regions for RNN sequence generation, QuPath digital pathology software was used to build modules for nuclear segmentation and cell classification. Nuclear segmentation was performed using Watershed cell detection based on segmentation parameters derived from images randomly selected from 9 subjects. Using the cell segmentation, a random forest classifier was trained to differentiate the nuclei into three classes (immune cells, tumor cells, and other, which included non-lymphocyte stromal tissue, areas obscured by melanin, or non-cell objects). The slide was divided into tiles, and thresholds were applied to each tile to determine the presence of relevant cell types. Tile size was empirically fixed to the width of 5 patches. Tiles with more than 65% of raw image pixels as white space background (pixel intensity value above 217) or 80% of segmented objects within the tile area classified as "other" were immediately discarded. These criteria, however, can be further adjusted as necessary for optimal performance. Then, points on the slide were randomly sampled from a 2D symmetric Gaussian distribution centered on the tile with a standard deviation equal to 3 times the patch width. A 500×500 patch centered on the randomly sampled point was analyzed, applying thresholds for maximum portion of white space background, minimum number of segmented tumor or immune cell nuclei, and maximum portion of segmented objects classified as "other." If the patch area passed the empirically determined thresholds, the downsampled area was added to the image sequence. Otherwise, the patch was discarded and a new point was randomly sampled. A maximum of six sequences (of length 20 each) were generated from each tile and if a sequence could not be generated after sampling 10,000 points, then the tile was discarded.

Feature Design

Figure 11:
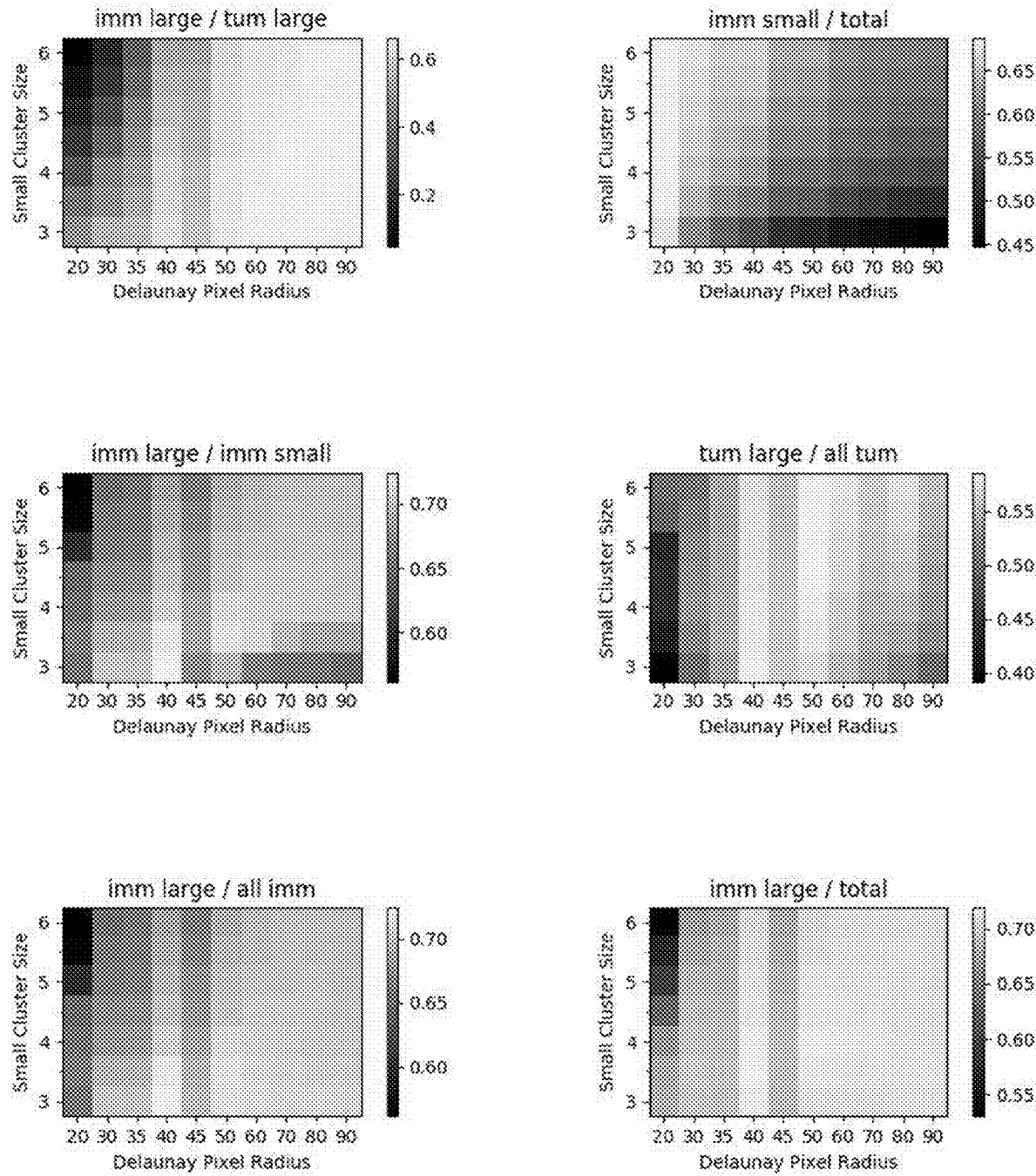
FIG. 11 is a set of Delaunay pixel radius graphs.

Morphology features measure the ratio of nuclear size in tumor and immune cells within the tile area, and the clustering features measure the ratio of cell density and cluster size based on Delaunay triangulation. The optimal parameters for the feature generation were selected using grid search of Delaunay pixel radius and minimum cluster size (FIG. 11). With reference to FIG. 11, The overall AUC for each Delaunay pixel radius and small cluster size within the Columbia set is shown for selection of configuration parameters in model training. The optimal features were then computed locally for every sequence based on information computed from all valid tiles immediately adjacent to the tile of the sequence being generated.

Analysis Pipeline

A deep neural network (DNN) architecture was designed consisting of a convolutional neural network (CNN) and a recurrent neural network (RNN). To avoid overfitting, the dropout procedure was used, which randomly sets a specified percentage of input units in every layer to zero and has been shown to outperform other regularization methods. In all experiments, the dropout rate was set to 0.7 and the learning rate was set to 0.005. The CNN input consisted of a 500×500×3 pixel patch from the raw H&E image at 40× magnification, downsampled to 100×100×3 pixels. The CNN output for each patch served as the RNN cell input. The sequence length was fixed to 20 image patches, and every sequence was normalized before input by subtracting the mean pixel intensity values and dividing by the standard deviation. The output of the RNN was appended with the features and processed through one (or in some embodiments more than one) fully connected layer to generate the final result.

Vote Aggregation

The classification output was aggregated from individual sequences across all images for a patient. Every sequence equally contributed to the final decision. The final decision for each patient's recurrence was made by computing the class (favorable vs. unfavorable) to which the majority of the sequences voted.

Statistics

Statistical analysis was completed using XLSTAT Version 2019.1.3 on Excel Version 15.0.5127 and GraphPad Prism Version 8.0.1. Statistical significance was defined as $P<0.05$. Receiver Operating Characteristic (ROC) curve analyses and standard univariable and multivariable Cox proportional hazards models were generated using the "Survival Analysis" feature on XLSTAT. Kaplan Meier (KM) curves were generated on GraphPad Prism and P values were calculated using Log-rank (Mantel-Cox) test.

First Test Population

Figure 12:
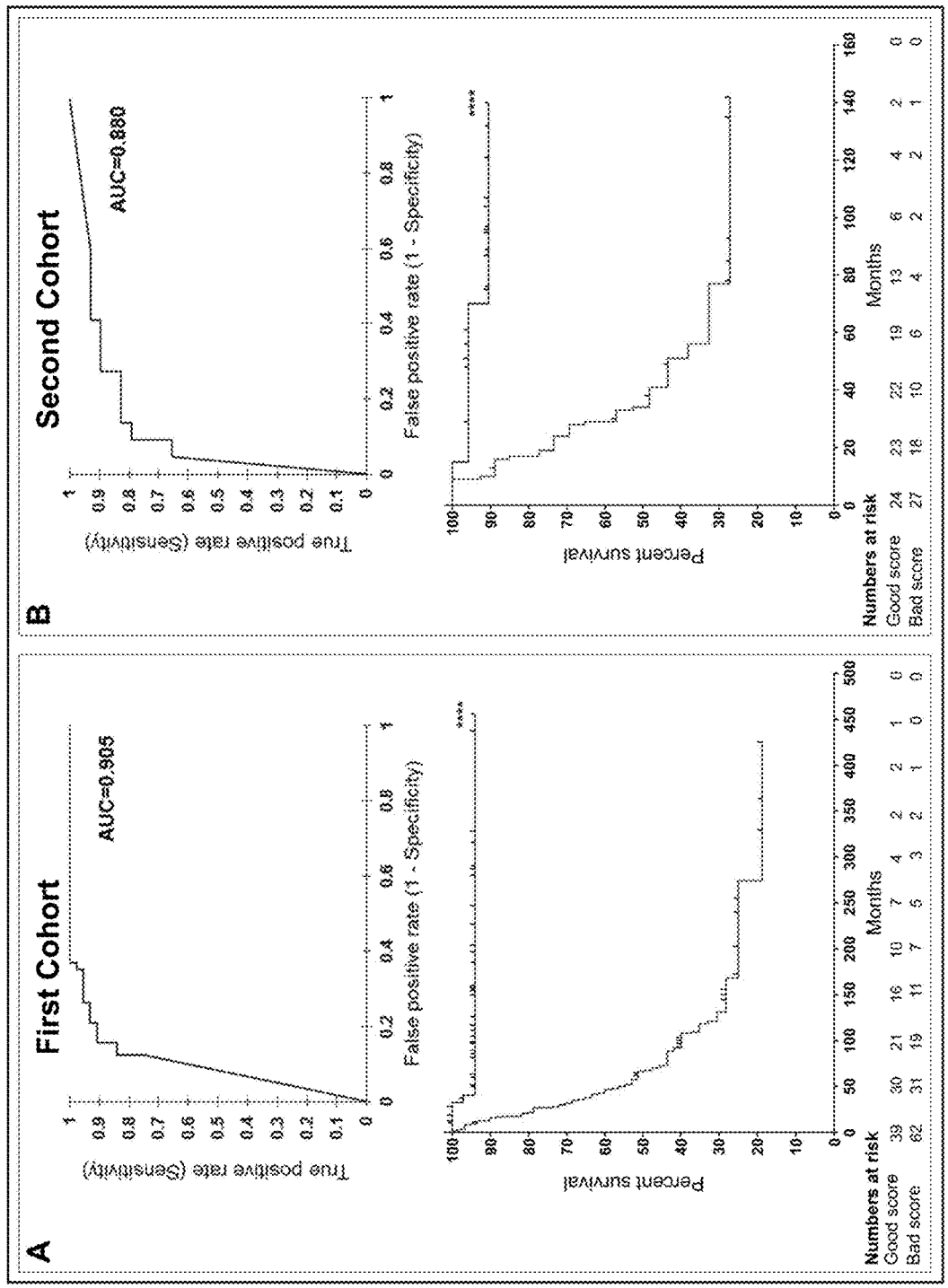
FIG. 12 is a graph of experimental results.

The first test population consisted of 118 samples. On pre-review, 7 were excluded because of heavy melanin and 7 were excluded because slides were cracked, images were blurred, or tissue was folded. Demographics are shown in Table 2 and Cox survival analysis using standard predictors is shown in Table 4 (training), Table 5 (validation cohort 1), and Table 6 (validation cohort 2). Patients were 50% male and 50% female with a median age of 60 years. Median follow up was 71.2 months. One slide was included for each patient and image sequences were generated followed by a prediction score as described above. A receiver operating characteristic (ROC) analysis was constructed and showed that the predictor strongly correlates with DMR (AUC=0.905). Disease specific survival is a key endpoint for adjuvant clinical trials and is the standard for prognostic biomarkers. A cutoff was selected to maximize sensitivity for recurrence with the goal of identifying a population that could be excluded from clinical trials, thereby increasing efficiency of accrual of patients at risk for death from melanoma, maximizing significance, and minimizing exposure of patients who do not need treatment. When this single cutoff was applied using KM analysis, the CNN classifier correlated significantly with DSS (p<0.0001, FIG. 12). When a multivariable analysis was performed, the DNN predictor correlated with DSS when other clinical predictors were included as co-variables (P<0.0001, Table 7).

TABLE 4

| Training set | | | |
|---|---|---|---|
| | Hazard ratio | 95% CI | P |
| Score | N/A | N/A | N/A |
| Stage*** | 3.4 | 1.8 to 6.2 | <0.001 |
| Gender | 0.67 | 0.29 to 1.6 | 0.347 |
| Age | 1.0 | 0.98 to 1.0 | 0.449 |
| Depth*** | 1.1 | 1.0 to 1.1 | <0.001 |
| Ulceration* | 2.6 | 1.2 to 5.6 | 0.014 |

TABLE 5

Validation Cohort 1

| | Hazard ratio | 95% CI | P |
|---|---|---|---|
| Score**** | 55 | 9.5 to 320 | <0.0001 |
| Stage | N/A | N/A | N/A |
| Gender | 0.60 | 0.33 to 1.1 | 0.087 |
| Age | 1.0 | 0.99 to 1.0 | 0.165 |
| Depth** | 1.2 | 1.0 to 1.4 | 0.009 |
| Ulceration | 1.4 | 0.78 to 2.6 | 0.258 |

TABLE 6

Validation Cohort 2

| | Hazard ratio | 95% CI | P |
|---|---|---|---|
| Score*** | 20 | 3.9 to 100 | <0.001 |
| Stage | 1.5 | 0.58 to 3.7 | 0.417 |
| Gender | 1.7 | 0.68 to 4.2 | 0.257 |
| Age | 1.0 | 0.99 to 1.1 | 0.163 |
| Depth | 1.2 | 1.0 to 1.3 | 0.053 |
| Ulceration | 2.7 | 0.97 to 7.5 | 0.057 |

TABLE 7

| | Hazard ratio | 95% CI | P |
|---|---|---|---|
| Score**** | 58.5 | 10.8 to 316 | <0.0001 |
| Gender | 0.966 | 0.510 to 1.83 | 0.915 |
| Age | 1.03 | 1.00 to 1.06 | 0.029 |
| Depth** | 1.31 | 1.08 to 1.57 | 0.005 |
| Ulceration | 0.678 | 0.350 to 1.31 | 0.249 |

Second Test Population

The second validation cohort consisted of 56 patients. On pre-review, 4 patients were excluded because of excessive melanin and 1 patient was excluded due to a lack of tumor in the image. Demographics are shown in Table 3 and univariable Cox survival analysis using standard predictors is shown in Table 6. When the DNN predictor was evaluated in this patient set, the AUC value was 0.880. Using the same cutoff as for the first population, the classifier significantly correlated with DSS using KM analysis (p<0.0001, FIG. 12). 24 patients had a favorable prediction score, of whom 5 had DMR and 27 patients had an unfavorable prediction of whom 24 had DMR. When a multivariable analysis was performed, the DNN predictor correlated with DSS when other clinical predictors were included as co-variables (P<0.001, Table 8).

TABLE 8

| | Hazard ratio | 95% CI | P |
|---|---|---|---|
| Score*** | 23 | 3.7 to 140 | 0.001 |
| Stage | 1.4 | 0.49 to 3.9 | 0.538 |
| Gender | 1.4 | 0.52 to 3.7 | 0.514 |
| Age | 1.0 | 0.99 to 1.1 | 0.112 |
| Depth | 1.0 | 0.89 to 1.2 | 0.589 |
| Ulceration | 1.8 | 0.60 to 5.2 | 0.298 |

CONCLUSION

The disclosed method is based on a newly designed algorithm and includes adaptations to allow for exclusion of areas with less relevant information, namely both the labeling of irrelevant areas such as those containing high levels of pigment as "other," and the requirement for a minimal number of tumor and/or lymphocytes in each patch. In addition, the DNN method presented here includes features such as nuclear size and distribution of immune cells within the tumor that have a high probability of being predictive based on previous pathology literature. One advantage of the disclosed method is that it is robust to variable H&E stains from different institutions, demonstrating broad applicability and robustness of the algorithm.

The disclosed method is highly promising with AUC values of 0.905 and 0.880 in two independent validation sets and suggests an accurate AI-based biomarker with clinical application is possible to facilitate stratification for clinical trials and improve the care of patients with early stage melanoma. Such a biomarker would accelerate screening for adjuvant clinical studies for early stage melanoma patients.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a subject by administering a treatment to a subject identified as having a high probability of distant metastatic recurrence, wherein the probability of distant metastatic recurrence was determined by a process, comprising:
    acquiring at least one image of a tissue sample comprising a plurality of cells, taken from a subject;
    classifying each of the plurality of cells into categories;
    dividing the at least one image into a plurality of patches, each patch comprising multiple cells of the plurality of cells;
    assigning cells in each of the plurality of patches to one or more clusters using a clustering algorithm to produce clustering data for each patch, the clustering data comprising a cluster size;
    calculating a cell density of each of the plurality of patches;
    calculating values for a plurality of morphological features based on the patches; and
    calculating a distant metastatic recurrence probability based on the values, the cell density, and the clustering data.

2. The method of claim 1, wherein the patches are acquired at least in part by random sampling.

3. The method of claim 1, wherein the categories comprise tumor cells, non-tumor cells, or immune cells.

4. The method of claim 1, further comprising identifying a subset of the patches of the image meeting a criterion selected from the group consisting of no cells appearing in the patch and no tumor cells appearing in the patch; and
    discarding the subset of patches.

5. The method of claim 1, wherein the distant metastatic recurrence probability is calculated by at least one neural network.

6. The method of claim 1, wherein the patches are selected by calculating a cell density and comparing the cell density to a threshold.

7. The method of claim 1, wherein the morphological features comprise at least one of (Count of immune cells in "large" cluster)/(Total count of immune cells); (Count of immune cells in "large" cluster)/(Total count of tumor+ immune); (Count of immune cells in "large" cluster)/(Count of tumor cells in "large" cluster); (Count of immune cells in "large" cluster)/(Count of immune cells in "small" cluster); (Total count of immune cells)/(Total count of tumor+immune); (Immune cell total area)/(Tumor cell total area); and (Immune cell total area)/(Total Immune area+Tumor area).

8. The method of claim 1, wherein the distant metastatic recurrence probability is calculated by aggregating a set of votes for each patch in the plurality of patches based on the values.

9. The method of claim 1, wherein the at least one image comprises at least first and second images, the first and second images acquired from different body regions of the subject.

10. The method of claim 1, wherein the treatment is selected from the group consisting of Nivolumab, Perbrolizumab, Ipilimumab, Dabrafenib, Trametinib, Vermurafenib, high-dose interferon alfa, chemotherapy, surgical excision, and immunotherapy.

* * * * *